US006202646B1

(12) United States Patent
Camodeca et al.

(10) Patent No.: US 6,202,646 B1
(45) Date of Patent: Mar. 20, 2001

(54) DETECTION DEVICE FOR VERIFYING THE PROPER INTUBATION OF AN ENDOTRACHEAL TUBE

(75) Inventors: Timothy F. Camodeca, Hampshire; James M. Flory, Roselle; Mark A. Kauth, Elgin, all of IL (US)

(73) Assignee: Para Products Incorporated, Roselle, IL (US)

( * ) Notice: Subject to any disclaimer, the term of this patent is extended or adjusted under 35 U.S.C. 154(b) by 0 days.

(21) Appl. No.: 09/219,390

(22) Filed: Dec. 23, 1998

(51) Int. Cl.[7] .................................................. A61M 16/00
(52) U.S. Cl. ................................ 128/207.14; 128/207.15; 128/200.26
(58) Field of Search ........................ 128/207.14, 207.15, 128/205.23, 202.22, 202.27, 200.26; 604/100

(56) References Cited

U.S. PATENT DOCUMENTS

| Re. 35,595 | 8/1997 | Six . | |
|---|---|---|---|
| 2,904,033 | 9/1959 | Shane . | |
| 4,446,864 | * 5/1984 | Watson et al. .................. | 128/207.14 |
| 4,953,547 | 9/1990 | Poole, Jr. . | |

(List continued on next page.)

OTHER PUBLICATIONS

1st Response Manual Resuscitator brochure, Smiths Industries, Jun. 1996.
Ambu TubeChek brochure, by Ambu, Inc., 1994.
Comparison of Self Inflating Bulb and Expired CO2 to Confirm Endotracheal Placement after Emergency Intubation, C.L. Kaper et al., 1996.
Practical Uses of the TubeChek in a Trauma Patient, Trauma Anesthesia Quarterly, May 1996.
Endotracheal Tuve Confirmation Accuracy Using the Bulb Esophageal Detector Device, Kevin Easton et al., Jul. 1996.
The Esophageal Detector Device: Summary of the Current Articles in the Literature, Tim Wolfe.

Primary Examiner—John G. Weiss
Assistant Examiner—V. Srivastava
(74) Attorney, Agent, or Firm—Lee, Mann, Smith, McWilliams, Sweeney & Ohlson

(57) ABSTRACT

A detection device adapted to be attached to the distal end of an endotracheal tube for verifying the proper intubation of the endotracheal tube within the airway of a patient. The detection device includes a housing having a proximal end, a distal end and a hollow bore extending through the housing from the proximal end to the distal end. The bore forms a proximal orifice at the proximal end of the housing and a distal orifice at the distal end of the housing. A plunger having a proximal end and a distal end extends through the distal orifice of the housing such that the proximal end of the plunger is located in the bore in sealing engagement with the housing. The plunger is selectively slidable within the bore along a longitudinal axis. A gripping member is attached externally to the housing adjacent to the proximal end of the housing. An adapter member having a ninety degree passageway is attached to the proximal end of the housing and to the distal end of the endotracheal tube such that the longitudinal axis along which the plunger is withdrawn from the housing is located at an angle of approximately ninety degrees to the endotracheal tube. The gripping member at the proximal end of the housing is adapted to be gripped with a first hand and the distal end of the plunger is adapted to be gripped with a second hand to facilitate withdrawal of the plunger from the housing to verify the proper placement of the endotracheal tube.

19 Claims, 2 Drawing Sheets

U.S. PATENT DOCUMENTS

| | | |
|---|---|---|
| 5,005,572 | 4/1991 | Raemer et al. . |
| 5,031,613 | 7/1991 | Smith et al. . |
| 5,135,490 | 8/1992 | Strickland . |
| 5,201,707 | 4/1993 | Kanai . |
| 5,203,320 | 4/1993 | Augustine . |
| 5,246,012 | 9/1993 | Strickland . |
| 5,279,289 * | 1/1994 | Kirk .............................. 128/205.23 |
| 5,309,903 | 5/1994 | Long . |
| 5,329,921 | 7/1994 | Socaris et al. . |
| 5,331,967 | 7/1994 | Akerson . |
| 5,400,770 | 3/1995 | Nakao et al. . |
| 5,431,152 | 7/1995 | Flam et al. . |
| 5,487,731 | 1/1996 | Denton . |
| 5,499,625 | 3/1996 | Frass et al. . |
| 5,509,408 | 4/1996 | Kurtis . |
| 5,591,130 | 1/1997 | Denton . |
| 5,620,004 | 4/1997 | Johansen . |
| 5,694,929 | 12/1997 | Christopher . |
| 5,890,488 * | 4/1999 | Burden ............................ 128/200.26 |
| 5,954,636 * | 9/1999 | Schwartz et al. .................... 600/120 |

* cited by examiner

DETECTION DEVICE FOR VERIFYING THE PROPER INTUBATION OF AN ENDOTRACHEAL TUBE

BACKGROUND OF THE INVENTION

The present invention is directed to a detection device adapted to be attached to the distal end of an endotracheal tube for verifying the proper intubation of the endotracheal tube within the airway of a patient, and in particular to a detection device having a housing with a gripping member at the proximal end of the housing and a plunger that is adapted to be withdrawn from the housing along a longitudinal axis that is disposed generally at a right angle to the endotracheal tube.

Endotracheal tubes are intended to be intubated within the trachea of a patient in order to ventilate the patient. The trachea is a relatively rigid tube that forms an airway for passing air to the lungs. The esophagus is a flexible muscular tube located between the trachea and the spinal cord that leads to the stomach. Thus the trachea is an airway passage to the lungs and the esophagus is a passage to the stomach for food and fluids. In order to ventilate a patient it is imperative that the endotracheal tube be intubated within the trachea that forms the airway, rather than within the esophagus. Even when the endotracheal tube is located within the trachea, as opposed to the esophagus, it is also important that the endotracheal tube be properly positioned within the trachea.

The anatomical differences between the relatively rigid trachea and the relatively flexible esophagus have led to the development of two general types of devices for verifying the proper placement of an endotracheal tube within the airway or trachea of a patient. These are the bulb-type device and the syringe-type device. Once the endotracheal tube has been intubated, the bulb-type device requires the medical attendant to squeeze the bulb of the bulb-type device prior to attaching the bulb-type device to the distal end of the endotracheal tube. After attachment, the bulb is released, and the bulb will try to expand and draw air through the endotracheal tube into the bulb. If the endotracheal tube is improperly intubated within the esophagus, the flexible wall of the esophagus will collapse and thereby prevent air from flowing through the endotracheal tube into the bulb and thereby preventing the bulb from fully expanding. If the endotracheal tube is properly intubated in the trachea, the rigid wall of the trachea will not collapse and the bulb will draw air through the endotracheal tube and the bulb will fully reexpand.

Use of the bulb-type device has provided false readings. Such false readings have been obtained when the medical attendant fails to squeeze the bulb before attaching the bulb-type device to the endotracheal tube, but instead squeezes the bulb after attachment to the endotracheal tube such that fifty to sixty milliliters of air are introduced into the patient. If the endotracheal tube was improperly intubated within the esophagus, the air pocket formed by the introduced air does not allow the esophagus to collapse properly to provide an indication that the endotracheal tube is improperly placed in the esophagus.

The syringe-type device does not require the pre-squeezing of a bulb and the use of the syringe-type device results in negligible false readings. The syringe-type device requires the medical attendant to attach the device to the distal end of the endotracheal tube and then pull back on the plunger of the syringe. If the endotracheal tube is properly intubated in the trachea, the plunger will pull back easily. If the endotracheal tube is improperly intubated in the esophagus the plunger will draw a vacuum collapsing the esophagus and thereby making withdrawal of the plunger difficult.

Prior syringe-type devices have caused endotracheal tubes that are initially properly intubated and properly positioned within the trachea to become misplaced within the trachea, that is, inserted too far or not inserted far enough into the trachea. The plungers of prior syringe-type devices are orientated generally coaxially to the distal end of the endotracheal tube, such that the withdrawal force applied to the plunger also acts to withdraw the endotracheal tube from the patient. Withdrawal of the endotracheal tube from the trachea by as little as one or two centimeters can make the difference between a properly placed endotracheal tube and a second attempt at intubation. Thus the bulb-type devices and the prior syringe-type devices both expose the patient to the risk of an unwanted extubation of an endotracheal tube and a second intubation of the endotracheal tube. The present invention greatly reduces these risks.

SUMMARY OF THE INVENTION

A detection device adapted to be attached to the distal end of an endotracheal tube for verifying the proper intubation of the endotracheal tube within the trachea or airway of a patient. The detection device comprises a housing having a proximal end and distal end. The housing includes a hollow bore having a central longitudinal axis extending through the housing from the proximal end to the distal end of the housing. The bore forms a proximal orifice at the proximal end of the housing and a distal orifice at the distal end of the housing. A plunger having a proximal end and a distal end extends through the distal orifice of the housing such that the proximal end of the plunger is located within the bore of the housing. The proximal end of the plunger sealingly engages the housing and is selectively slidable within the bore with respect to the housing. The distal end of the plunger is adapted to be grasped by hand to manually withdraw the plunger from the housing along the central longitudinal axis of the bore. A gripping member is attached to the housing adjacent to the proximal end of the housing and is spaced apart from the distal end of the housing.

A ninety-degree adapter member includes a proximal end that is adapted to be attached to the distal end of the endotracheal tube and a distal end that is adapted to be attached to the proximal end of the housing. The adapter member includes a passageway formed by a first hollow bore that forms a proximal port located at the proximal end of the adapter member and a second hollow bore that forms a distal port at the distal end of the adapter member. The second bore is adapted to place the first bore in fluid communication with the bore of the housing. The first bore of the adapter member includes a central longitudinal axis that is disposed at an angle of approximately ninety-degrees to the central longitudinal axis of the bore of the housing along which the syringe is withdrawn.

The proximal end of the housing is adapted to be attached to the distal end of the endotracheal tube by the adapter member such that a medical attendant may simultaneously grip the gripping member attached to the proximal end of the housing, the adapter member, and the distal end of the endotracheal tube with a first hand to secure all three components together and to hold them stationary while the medical attendant withdraws the plunger with a second hand. The plunger is withdrawn along the central longitudinal axis of the bore of the housing at an angle of generally ninety-degrees to the central axis of the endotracheal tube to limit inadvertent movement of the housing and endotracheal tube as the plunger is withdrawn from the housing.

BRIEF DESCRIPTION OF THE DRAWING FIGURES

DETAILED DESCRIPTION OF THE PREFERRED EMBODIMENTS

Figure 1:
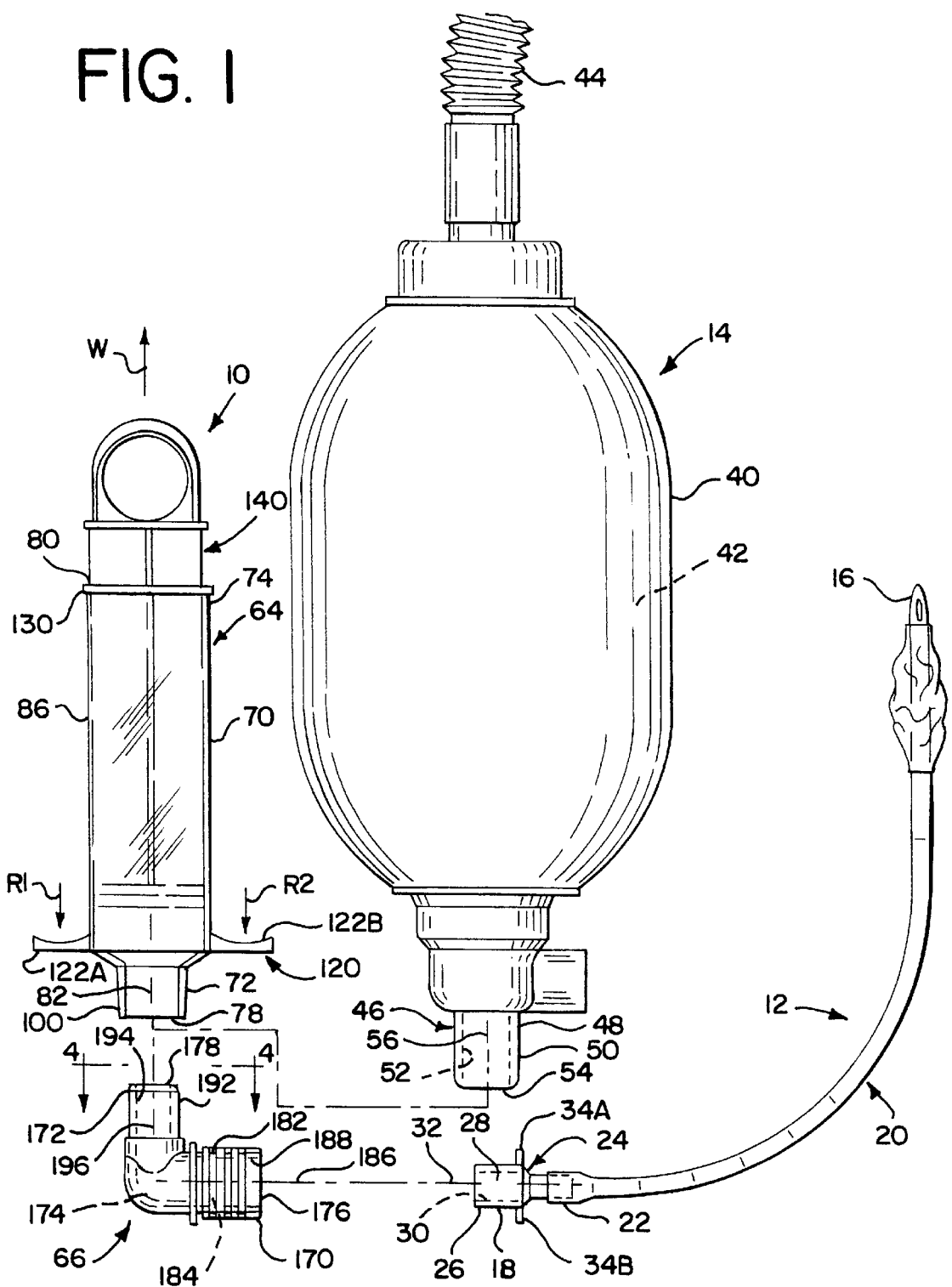
FIG. 1 is a diagrammatic view showing the detection device of the present invention in connection with an endotracheal tube and a resuscitation bag.

The detection device 10 of the present invention is shown in FIG. 1 in connection with an endotracheal tube 12 and a resuscitation bag 14. The endotracheal tube 12 includes a proximal end 16 and a distal end 18. The proximal end 16 of the endotracheal tube 12 is adapted to be inserted or intubated into the airway of a patient formed by the trachea of a patient while the distal end 18 of the endotracheal tube 12 remains located outside of the patient. The endotracheal tube 12 includes a hollow flexible tube 20 having a port at the distal end 18 of the endotracheal tube 12 and an end 22. The endotracheal tube 12 also includes a connector member 24 that is connected to the end 22 of the tube 20. The connector member 24 includes a generally cylindrical tube 26. The cylindrical tube 26 includes an outer generally cylindrical surface 28 and a linear generally cylindrical bore 30 having a linear central longitudinal axis 32. The bore 30 is in fluid communication with a passageway of the tube 20. The outer cylindrical surface 28 of the connector member 24 has a diameter of approximately 0.597 inches at its outer end with a 0.75 degree taper toward the outer end, which is a generally standard size for the distal end of endotracheal tubes. A pair of ears 34A and B are attached to the cylindrical tube 26 and extend outwardly therefrom.

The resuscitation bag 14 includes a flexibly squeezable bag 40 having a hollow chamber 42. The distal end of the bag 40 is connected to a tube 44 that provides a supply of air or oxygen to the chamber 42 of the bag 40. A connector member 46 is attached to the proximal end of the bag 40. The resuscitation bag 14 typically also includes a one-way valve (not shown) that provides selective fluid communication between the chamber 42 and the connector member 46. The connector member 46 includes a generally cylindrical tube 48. The tube 48 includes a generally cylindrical wall 50 having a generally linear and cylindrical bore 52 that forms a port 54 at the end of the tube 48. The bore 52 includes a linear central longitudinal axis 56. The bore 52 tapers slightly inwardly from the port 54 toward the bag 40 at an approximate angle of 0.75 degrees. Thus the diameter of the bore 52 decreases slightly as the bore 52 extends inwardly from the port 54. The diameter of the port 54 is approximately 0.610 inches such that the cylindrical tube 26 of the connector member 24 of the endotracheal tube 12 can be removably attached to the tube 48 of the connector member 46 of the resuscitation bag 14 by longitudinally sliding the tube 26 of the endotracheal tube 12 within the bore 52 of the tube 48 of the resuscitation bag 14. The cylindrical surface 28 of the tube 26 engages the inner surface of the cylindrical wall 50 of the tube 48 to form a releasable press-fit friction connection therebetween.

Figure 2:
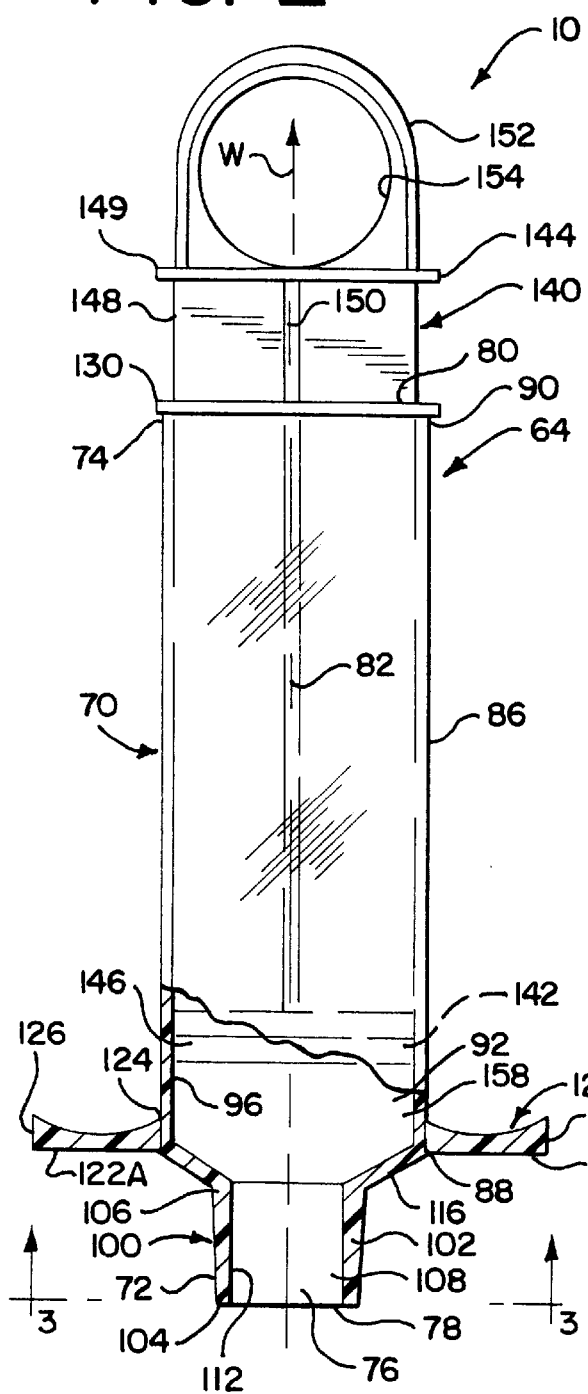
FIG. 2 is a side elevational view of the syringe of the detection device shown partially in cross section.

The detection device 10 includes a syringe 64 and an adapter member 66. As best shown in FIG. 2, the syringe 64 includes a housing 70 having a proximal end 72 and a distal end 74. The housing 70 includes a hollow bore 76 that forms a generally circular proximal orifice 78 at the proximal end 72 of the housing 70 and a generally circular distal orifice 80 at the distal end 74 of the housing 70. The bore 76 extends generally linearly between the proximal orifice 78 and the distal orifice 80 and includes a linear central longitudinal axis 82.

The housing 70 includes a generally cylindrical and tubular barrel 86 that extends from a first end 88 to a second end 90. The second end 90 is located at the distal end 74 of the housing 70 and includes the distal orifice 80. The barrel 86 includes a hollow generally cylindrical bore 92 that extends from the first end 88 to the second end 90 of the barrel 86 and that forms the distal orifice 80. The bore 92 forms a portion of the bore 76 of the housing 70 and extends concentrically along the central longitudinal axis 82. The bore 92 forms a generally cylindrical interior wall 96. The bore 92 has an internal diameter of approximately 1.050 inches.

The housing 70 also includes a connector member 100 including a generally cylindrical tube 102. The tube 102 includes a first end 104 and a second end 106. The first end 104 is located at the proximal end 72 of the housing 70 and includes the proximal orifice 78. The tube 102 includes a linear bore 108 that extends from the proximal orifice 78 at the first end 104 to the second end 106 of the tube 102 The bore 108 forms a portion of the bore 76, is generally cylindrical, and extends concentrically along the central longitudinal axis 82. The tube 102 includes an interior wall surface 112 that is generally cylindrical and that tapers inwardly as the wall surface 112 extends from the first end 104 to the second end 106 of the tube 102. Thus the diameter of the proximal orifice 78 at the first end 104 of the cylindrical tube 102 is slightly larger than the diameter of the bore 108 at the second end 106 of the cylindrical tube 102. The diameter of the proximal orifice 78 is preferably at least approximately one-half inch and is preferably approximately 0.61 inch. The internal tapered wall surface 112 is preferably tapered at an angle of approximately 0.75 degrees with respect to the central longitudinal axis 82. The second end 106 of the tube 102 is integrally connected to the first end 88 of the barrel 86 by an annular conical wall 116 such that the bore 108 is in fluid communication with the bore 92. The diameter of the proximal orifice 78 and the bore 108 are sized such that the connector member 100 is adapted, if desired, to removably connect the proximal end 72 of the housing 70 directly to the distal end 18 of the endotracheal tube 12 by inserting the cylindrical tube 26 of the endotracheal tube 12 through the proximal orifice 78 and into the bore 108 of the connector member 100 whereby the internal tapered wall 112 of the connector member 100 will grip the distal end 18 of the endotracheal tube 12 in a press-fit friction connection.

Figure 3:
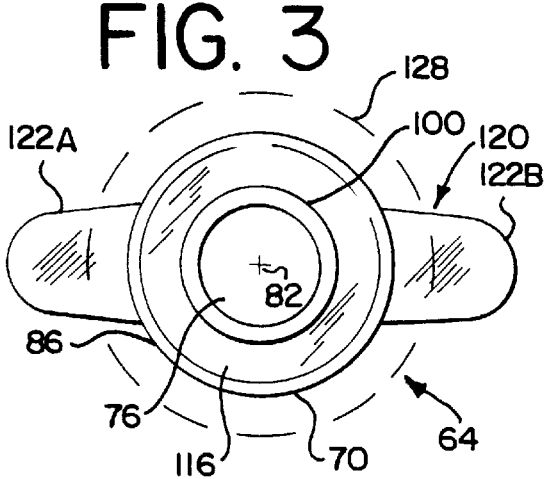
FIG. 3 is a an end view of the syringe taken along lines 3—3 of FIG. 2 and also showing a second embodiment of the gripping member in phantom lines.

A finger gripping member 120 is attached externally to the housing 70 at the first end 88 of the barrel 86. As shown in FIGS. 2 and 3, the gripping member 120 includes a pair of radially outwardly extending tabs 122A and B. The tabs 122A–B each include a first end 124 attached to the first end 88 of the barrel 86 and a second end 126 spaced generally radially outwardly from the barrel 86. The tabs 122A–B are respectively located on diametrically opposite sides of the housing 70. If desired the gripping member 120 may be formed in other configurations such as by a pair of finger loops or rings located on diametrically opposite sides of the housing 70, or a generally annular ring 128 that extends around the housing 70 as shown in phantom lines in FIG. 3. The gripping member 120 is located adjacent the proximal end 72 of the housing 70 and spaced apart from the distal end 74. If desired, a second gripping member 130, such as a pair of tabs or an annular ring, may be attached to the distal end 74 of the housing 70.

The syringe 64 also includes a plunger 140 having a proximal end 142 and a distal end 144. The plunger 140 includes an elastomeric disc-like member 146 at the proximal end 142 that is generally circular and that is adapted to slidably and sealingly engage the interior cylindrical wall 96 formed by the bore 92 of the barrel 86. The plunger 140 also includes a generally linear and elongate shaft 148 that extends from the disc-like member 146 to a circular disc 149 located at the distal end 144 of the plunger 140. The shaft 148 may comprise four generally planar webs arranged in an X-shaped configuration. The distal end 144 of the plunger 140 is adapted to be manually grasped by hand. The plunger 140 includes a linear central longitudinal axis 150 that is coaxial with the central longitudinal axis 82 of the housing 70. If desired, the distal end 144 of the plunger 140 may include a finger loop 152 having an aperture 154. The plunger 140 extends through the distal orifice 80 of the housing 70 such that the disc-like member 146 at the proximal end 142 of the plunger 140 is located within the bore 92 of the barrel 86. The plunger 140 is selectively slidable in a generally linear direction with respect to the housing 70 along the central longitudinal axis 82 of the housing 70. The disc-like member 146 of the plunger 140 creates a hollow chamber 158 within the bore 92 that extends between the disc-like member 146 and the first end 88 of the barrel 86. The size of the chamber 158 increases as the plunger 140 is withdrawn from the bore 92 of the housing 70 in a direction shown by the arrow marked "W" in FIG. 2, and the size of the chamber 158 decreases in size as the plunger 140 is inserted into the bore 92 of the housing 70. The barrel 86 is preferably sized such that the chamber 158 will have a volume of approximately sixty cubic centimeters when the proximal end 142 of the plunger 140 is located at the distal end 74 of the housing 70.

Figure 4:
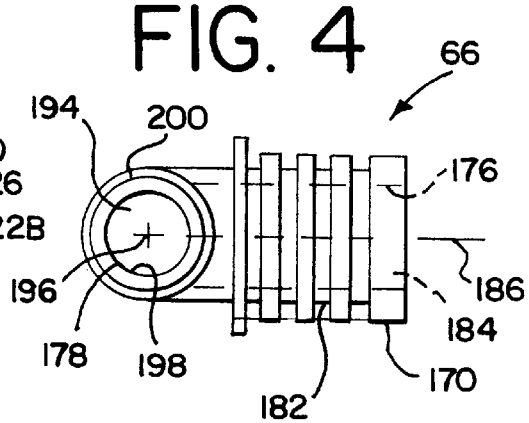
FIG. 4 is a side elevational view of the adapter member of the detection device taken along lines 4—4 of FIG. 1.

The adapter member 66, as best shown in FIGS. 1 and 4, is generally configured as a ninety-degree or right-angle elbow. The adapter member 66 includes a proximal end 170 and a distal end 172. The adapter member 66 includes a passageway 174 that forms a proximal port 176 at the proximal end 170 and a distal port 178 at the distal end 172 of the adapter member 66. The adapter member 66 includes a first generally cylindrical tube 182 having a generally cylindrical bore 184 that forms a portion of the passageway 174 and that forms the proximal port 176. The first bore 184 includes a generally linear central longitudinal axis 186 and forms a generally cylindrical interior surface 188 within the first tube 182. The diameter of the proximal port 176 and of the interior cylindrical surface 188 of the first bore 184 are sized such that the distal end 18 of the endotracheal tube 12 may be inserted through the proximal port 176 and into the fist bore 184 such that the cylindrical surface 28 of the endotracheal tube 12 will removably engage the interior cylindrical surface 188 of the first bore 184 in a press-fit friction connection.

The adapter member 66 also includes a second generally cylindrical tube 192 that includes a generally cylindrical second bore 194 that forms a portion of the passageway 174. The second bore 194 forms the distal port 178 and includes a generally linear central longitudinal axis 196. The second bore 194 also includes an interior generally cylindrical surface 198. The second bore 194 is in fluid communication with the first bore 184. The second cylindrical tube 192 includes an exterior generally cylindrical surface 200. The exterior cylindrical surface 200 has a diameter of approximately 0.600 inches at its outer end and tapers inwardly toward the end at an approximate angle of 0.75 degrees. The external cylindrical surface 200 is adapted to be inserted within the bore 108 of the connector member 100 of the housing 70 such that the external surface 200 engages the interior tapered wall 112 to form a press-fit friction connection thereby removably connecting the distal end 172 of the adapter member 66 to the proximal end 72 of the housing 70. The exterior cylindrical surface 200 of the adapter member 66 is also adapted to be removably connected to the connector member 46 of the resuscitation bag 14 by inserting the second cylindrical tube 192 through the port 54 and into the bore 52 of the connector 46 such that the exterior cylindrical surface 200 engages the cylindrical wall 50 to form a press-fit friction connection. The central longitudinal axis 196 of the second tube 192 may be disposed at an angle of from approximately 45° to approximately 135° to the central longitudinal axis 186 of the first tube 182, and is preferably disposed at an angle of approximately ninety degrees (approximately a right angle) to the central longitudinal axis 186 of the first tube 182. The adapter member 66 is a standard component made available for use in connecting endotracheal tubes to resuscitation bags.

When the second cylindrical tube 192 of the adapter member 66 is connected to the connector member 100 at the proximal end 72 of the housing 70, the central longitudinal axis 196 of the second bore 194 is generally coaxial to the central longitudinal axis 82 of the housing 70, and the central longitudinal axis 186 of the second cylindrical tube 192 is disposed at an angle of from approximately 45° to approximately 135°, and preferably approximately 90°, relative to the central longitudinal axis 186 of the first cylindrical tube 182, and the passageway 174 is in fluid communication with the chamber 158.

As shown diagrammatically in FIG. 1, the distal end 18 of the endotracheal tube 12 is adapted to be inserted into the bore 52 of the connector member 46 of the resuscitation bag 14 such that the endotracheal tube 12 is removably connected in fluid communication with the resuscitation bag 14. The distal end 18 of the endotracheal tube 12 may also be inserted into the bore 108 of the connector member 100 of the housing 70 such that the endotracheal tube 12 is removably connected in direct fluid communication with the syringe 64. The distal end 18 of the endotracheal tube 12 may also be inserted into the first bore 184 of the adapter member 66 such that the endotracheal tube 12 is removably connected in fluid communication with the passageway 174 of the adapter member 66.

The second cylindrical tube 192 of the adapter member 66 is adapted to be inserted within the bore 108 of the connector member 100 of the housing 70 such that the adapter member 66 is removably connected in fluid communication with the chamber 158 of the syringe 64. The second cylindrical tube 192 of the adapter member 66 is also adapted to be inserted into the bore 52 of the connector member 46 of the resuscitation bag 14 such that the passageway 174 of the adapter member 66 is in fluid communication with the resuscitation bag 14.

In operation, the proximal end 16 of the endotracheal tube 12 is inserted or intubated within the airway of the patient formed by the trachea while the distal end 18 of the endotracheal tube 12 remains outside of the patient. The second cylindrical tube 192 of the adapter member 66 is inserted through the proximal orifice 78 and into the bore 108 of the housing 70 of the syringe 64 thereby removably connecting the adapter member 66 to the syringe 64. The plunger 140 is fully inserted into the bore 92 of the barrel 86 of the housing 70. While the distal end 18 of the endotracheal tube 12 is held in a stationary position, the first cylindrical tube 182 of the adapter member 66 is slid downwardly over and around the cylindrical tube 26 at the distal end 18 of the endotracheal tube 12 to thereby removably connect the distal end 18 of the endotracheal tube 12 in fluid communication with the passageway 174 of the adapter member 66 and the chamber 158 of the syringe 64. The central longitudinal axis 186 of the first cylindrical tube 182 is thereby generally coaxial with the central longitudinal axis 32 of the bore 30 at the distal end 18 of the endotracheal tube 12. The central longitudinal axis 82 of the housing 70 and the coaxial central longitudinal axis 150 of the plunger 140 are thereby disposed at an angle of approximately ninety degrees to the central longitudinal axis 32 of the bore 30 at the distal end 18 of the endotracheal tube 12.

The first cylindrical tube 182 of the adapter member 66 is placed against the palm of a first hand of a medical attendant and the index finger of the first hand is wrapped around the tab 122A of the gripping member 120 and the middle finger of the first hand is wrapped around the tab 122B of the gripping member 120. The ring finger and little finger of the first hand of the medical attendant are then wrapped around the distal end 18 of the endotracheal tube 12. The thumb of the first hand is placed along the second cylindrical tube 192 of the adapter member 66. The first hand of the medical attendant thereby grips the gripping member 120, the proximal end 72 of the housing 70, the adapter member 66, and the distal end 18 of the endotracheal tube 12 to retain them in a stationary position relative to the patient. The distal end 144 of the plunger 140 is then grasped with the second hand of the medical attendant and the plunger 140 is withdrawn from the bore 92 of the housing 70 in a linear direction as shown by the arrow W along the central longitudinal axis 82, thereby sliding the proximal end 142 of the plunger 140 from the first end 88 of the barrel 86 toward the second end 90 of the barrel 86 and enlarging the size of the chamber 158.

If the endotracheal tube 12 is properly intubated within the trachea of the patient, the plunger 140 will be easily withdrawn from the housing 70 as air from the trachea will flow through the endotracheal tube 12 into the chamber 158. However, if the endotracheal tube 12 was improperly intubated within the esophagus of the patient, the wall of the esophagus will collapse around the proximal end 16 of the endotracheal tube 12 as the plunger 140 is withdrawn from the housing 70 to prevent air from entering the endotracheal tube 12 and the chamber 158. The plunger 140 is thereby drawing a vacuum as the plunger 140 is withdrawn from the housing 70 making withdrawal of the plunger 140 difficult and indicating improper intubation within the esophagus.

As shown in FIG. 1, when the plunger 140 is withdrawn from the housing 70 in the direction of the arrow marked "W" and with a force equal to "W", the force W must be resisted by an equal and opposite force consisting of the sum of the force R1 created by the ring finger of the first hand and the force R2 created by the middle finger of the first hand upon the gripping member 120. When the withdrawal force W applied by the second hand of the medical attendant exactly equals the sum of the resisting forces R1 and R2 applied by the first hand of the medical attendant on the gripping member 120, the housing 70, adapter member 66 and endotracheal tube 12 will remain stationary with respect to the patient. It will be appreciated that exactly balancing the resisting forces R1 and R2 to equal the withdrawal force W is difficult under the best of conditions, and is nearly impossible when this procedure is performed in a moving ambulance.

When the sum of the resisting forces R1 and R2 do not exactly equal the withdrawal force W, the housing 70 will move in one direction or the other along the central longitudinal axis 82. As the central longitudinal axis 82 is disposed generally at a right angle to the central longitudinal axis 32 of the connector member 24 at the distal end 18 of the endotracheal tube 12, movement of the housing 70 along the central longitudinal axis 82 results in some transverse movement of the distal end 18 of the endotracheal tube 12 and bending of the tube 20. However, such movement of the housing 70 will not cause movement of the endotracheal tube 12 along its longitudinal axis, either further into the trachea or out of the trachea, and will not cause any movement of the proximal end 16 of the endotracheal tube 12 with respect to the patient.

On the other hand, with the prior syringe-type devices, the central longitudinal axis of the syringe is located generally coaxial with the central longitudinal axis 32 of the connector member 24 of the endotracheal tube 12. In this arrangement any movement of the housing of the syringe due to an imbalance between the withdrawal and resisting forces applied to the syringe will result in longitudinal movement of the syringe and in longitudinal movement of the endotracheal tube 12, thereby either inserting the endotracheal tube 12 and its distal end 18 further into the trachea or withdrawing the endotracheal tube 12 and its proximal end 16 from the trachea. Such undesired longitudinal movement of the endotracheal tube 12 can result in a need to extubate the endotracheal tube 12 and to reintubate the endotracheal tube 12.

Once it has been verified that the endotracheal tube 12 is properly positioned within the trachea, the housing 70 of the syringe 64 is separated from the adapter member 66 in a direction generally transverse to the central longitudinal axis 32 of the distal end 18 of the endotracheal tube 12 along the axis 82, again preventing any longitudinal movement of the endotracheal tube 12. The second cylindrical tube 192 of the adapter member 66 can then be attached to the connector member 46 of the resuscitation bag 14 such that the resuscitation bag 14 is in fluid communication with the endotracheal tube 12 and such that the resuscitation bag 14 may be utilized to ventilate the patient.

Various features of the invention have been particularly shown and described in connection with the illustrated embodiments of the invention, however, it must be understood that these particular arrangements merely illustrate, and that the invention is to be given its fullest interpretation within the terms of the appended claims.

What is claimed is:

1. A detection device adapted to be attached to the distal end of an endotracheal tube for verifying the proper intubation of the endotracheal tube within the airway of a patient, said detection device comprising:

a housing having a proximal end and a distal end, said housing including a hollow bore extending through said housing from said proximal end to said distal end of said housing, said bore forming a proximal orifice at said proximal end of said housing and a distal orifice at said distal end of said housing;

a plunger having a proximal end and a distal end, said plunger extending through said distal orifice of said housing such that said proximal end of said plunger is located within said bore of said housing, said proximal end of said plunger being selectively slidable within said bore with respect to said housing, said distal end of said plunger adapted to be manually grasped; and a first gripping member attached to said housing adjacent to said proximal end of said housing;

whereby said proximal end of said housing is adapted to be attached to the distal end of the endotracheal tube such that said bore of said housing is in fluid communication with the endotracheal tube, and said gripping member is adapted to enable said proximal end of said housing to be manually grasped to limit inadvertent movement of said housing while said plunger is slidably withdrawn from said bore of said housing through said distal orifice of said housing.

2. The detection device of claim 1 wherein said housing includes a barrel having a first end and a second end, said bore including a hollow first bore portion extending through said barrel from said first end to said second end of said barrel, said first bore portion forming said distal orifice at said second end of said barrel, and a connector member located at said proximal end of said housing having a first end and a second end, said bore including a hollow second bore portion extending through said connector member from said first end to said second end of said connector member, said second end of said connector member being attached to said first end of said barrel such that said first bore portion is in fluid communication with said second bore portion, said second bore portion forming said proximal orifice at said first end of said connector member.

3. The detection device of claim 2 wherein said first gripping member is attached to said first end of said barrel of said housing.

4. The detection device of claim 2 wherein said second bore portion of said connector member has a diameter of at least one-half inch.

5. The detection device of claim 4 wherein said connector member comprises a tube extending from said first end to said second end of said connector member, said tube having an inner surface that tapers inwardly from said first end of said connector member toward said second end of said connector member.

6. The detection device of claim 1 wherein said bore of said housing includes a generally linear central longitudinal axis, and said first gripping member extends outwardly from said housing generally transversely to said central longitudinal axis.

7. The detection device of claim 1 wherein said first gripping member includes a first tab having a first end attached to said housing and a second end located outwardly from said housing.

8. The detection device of claim 7 wherein said first gripping member includes a second tab having a first end attached to said housing and a second end located outwardly from said housing, said first and second tabs being respectively located on diametrically opposite sides of said housing.

9. The detection device of claim 1 wherein said first gripping member comprises a generally annular ring extending around said housing.

10. The detection device of claim 1 wherein said first gripping member comprises a finger loop.

11. The detection device of claim 1 including a second gripping member attached to said housing at said distal end of said housing.

12. The detection device of claim 1 wherein said proximal orifice of said housing has a diameter of at least one-half inch.

13. The detection device of claim 1 wherein said proximal orifice of said housing is adapted to receive the distal end of the endotracheal tube.

14. The detection device of claim 1 wherein said housing includes a barrel having a first end and a second end, said bore of said housing including a hollow first bore portion having a first linear central longitudinal axis that extends through said barrel, said first bore portion forming said distal orifice of said housing; and said detection device includes an adapter member having a proximal end, a distal end and a hollow first bore having a second linear central longitudinal axis, said hollow first bore of said adapter member forming a proximal port in said proximal end of said adapter member, said distal end of said adapter member adapted to be connected to said proximal end of said housing such that said bore of said adapter member is in fluid communication with said first bore portion of said housing and such that said second central longitudinal axis of said first bore of said adapter member is disposed at an angle to said first central longitudinal axis of said first bore portion of said housing.

15. The detection device of claim 14 wherein said second central longitudinal axis of said first bore of said adapter member is adapted to be disposed at an angle of between approximately forty-five degrees and approximately one-hundred thirty-five degrees relative to said first central longitudinal axis of said first bore portion of said housing.

16. The detection device of claim 14 wherein said second central longitudinal axis of said first bore of said adapter member is adapted to be disposed at an angle of approximately ninety degrees relative to said first central longitudinal axis of said first bore portion of said housing.

17. The detection device of claim 14 wherein said adapter member is removably connectable to said housing.

18. The detection device of claim 14 wherein said adapter member includes a second bore having a third linear central longitudinal axis, said second bore forming a distal port in said distal end of said adapter member, said second bore adapted to provide fluid communication between said first bore portion of said housing and said second bore of said adapter member, said third central longitudinal axis of said second bore being disposed at an angle relative to said second central longitudinal axis of said second bore of said adapter member.

19. The detection device of claim 18 wherein said third central longitudinal axis of said second bore of said adapter member is disposed at an angle of approximately ninety degrees relative to said second central longitudinal axis of said first bore of said adapter member.

* * * * *